(12) United States Patent
Kimberlin

(10) Patent No.: US 7,821,415 B1
(45) Date of Patent: Oct. 26, 2010

(54) PNEUMATICALLY OPERATED PATIENT BED MONITOR

(76) Inventor: Denver K. Kimberlin, 13140 S. 273rd East Ave., Coweta, OK (US) 74429

( * ) Notice: Subject to any disclaimer, the term of this patent is extended or adjusted under 35 U.S.C. 154(b) by 282 days.

(21) Appl. No.: 12/062,739

(22) Filed: Apr. 4, 2008

(51) Int. Cl.
*G08B 21/00* (2006.01)
*G01B 7/16* (2006.01)
*G01F 25/00* (2006.01)
*G01L 1/00* (2006.01)

(52) U.S. Cl. ........................................ 340/666; 73/763
(58) Field of Classification Search ................... 73/760, 73/763, 768, 773, 781; 340/539.12, 666, 340/667, 693.5
See application file for complete search history.

(56) References Cited

U.S. PATENT DOCUMENTS

| | | | |
|---|---|---|---|
| 3,209,089 A * | 9/1965 | Weissburg ................ 200/16 A |
| 3,894,206 A * | 7/1975 | Suzuki et al. ............. 200/85 A |
| 4,020,482 A | 4/1977 | Feldl |
| 4,137,116 A | 1/1979 | Miller |
| 4,175,263 A * | 11/1979 | Triplett et al. ............. 340/573.4 |
| 4,250,434 A * | 2/1981 | Valansot ..................... 315/362 |
| 4,336,533 A | 6/1982 | Wettach |
| 4,401,896 A | 8/1983 | Fowler et al. |
| 4,454,615 A | 6/1984 | Whitney |
| 4,483,030 A | 11/1984 | Flick et al. |
| 4,484,043 A | 11/1984 | Musick et al. |
| 4,565,910 A | 1/1986 | Musick et al. |
| 4,638,307 A * | 1/1987 | Swartout .................... 340/666 |
| 4,845,323 A * | 7/1989 | Beggs ....................... 200/85 R |
| 5,142,109 A * | 8/1992 | O'Meara et al. .......... 200/86 R |
| 5,767,774 A | 6/1998 | Wright et al. |
| 5,844,488 A | 12/1998 | Musick |
| 5,886,615 A * | 3/1999 | Burgess ..................... 338/114 |
| 6,078,261 A | 6/2000 | Davsko |
| 6,212,718 B1 | 4/2001 | Stolpmann et al. |
| 6,417,777 B2 | 7/2002 | Fitzgerald et al. |
| 6,583,727 B2 | 6/2003 | Nunome |
| 6,686,818 B1 * | 2/2004 | Weibler et al. ............. 333/231 |
| 6,771,190 B2 | 8/2004 | Gordon |
| 7,253,366 B2 | 8/2007 | Bhai |
| 7,436,299 B2 * | 10/2008 | Shieh et al. ................. 340/561 |
| 2004/0201487 A1 * | 10/2004 | Benson et al. ............. 340/666 |
| 2007/0057778 A1 * | 3/2007 | Prince et al. ............. 340/384.6 |
| 2007/0115121 A1 * | 5/2007 | Schleeh ..................... 340/562 |

* cited by examiner

Primary Examiner—Jennifer Mehmood
(74) Attorney, Agent, or Firm—Gable Gotwals

(57) ABSTRACT

A pneumatic patient bed monitor comprises a hermetically sealed flexible outer shell that contains a porous foam core having a certain volume of air. A flexible tube places the foam core in communication with a pneumatic pressure switch. The tube is hermetically sealed to both the outer shell and the switch. The pressure switch is in a normally open position. When a weight of a patient compresses the foam core, air contained in the foam core flows in a controlled manner into the tube, thereby causing a rise in pressure within the tube and actuating the pressure switch. When the weight of the patient is removed, air flows out of the tube in a controlled manner and back into the foam core, causing a drop in pressure within the tube and de-actuating the pressure switch. The foam core returns to its decompressed state.

14 Claims, 1 Drawing Sheet

PNEUMATICALLY OPERATED PATIENT BED MONITOR

REFERENCE TO PENDING APPLICATIONS

This application is not based upon any pending domestic or international patent applications.

FIELD OF INVENTION

This invention relates generally to patient alarms and monitoring systems and, more particularly, concerns devices and systems used to monitor bed patients in hospitals and other care-giving environments.

BACKGROUND OF THE INVENTION

In care-giving environments, many elderly and post-surgical patients are at a heightened risk of falling. Because falls increase the risk of additional injury, the patient requires monitoring by a caregiver. Various types of monitoring devices and systems have been developed, the most common type being an electronic monitor.

Electronic monitors sense an initial status of the patient and generate a signal when that status changes, for example, the patient has sat up in bed, left the bed, or risen from a chair. The monitor typically comprises an outer casing containing two electrode plates separated by a spacer. When external pressure is applied to the outer casing, the casing presses downward until the electrode plates make contact with one another through holes in the spacer. The connection indicates the patient is in the bed and causes an alarm to silence.

Although electronic monitors have captured 100% of the patient bed monitor market, the monitors have serious disadvantages. The monitors rely upon electrical leads and opposing conductive surfaces, both of which tend to wear or break in a relatively short time period. Because electrical circuitry is involved, the monitors cannot be used in certain patient environments and the potential for shock exists. Isolation circuits attempt to reduce the risk of shock but cannot eliminate the risk to the point at which Underwriters Laboratories certification may be obtained.

Another disadvantage of electronic monitors is the outer casing cannot be an enclosed envelope. In an enclosed envelope, entrapped air prevents the electrodes from coming into contact with one another. Therefore, an opening must be placed along a seam to allow entrapped air to escape. This opening, however, provides a passageway for contaminants to enter an interior of the monitor, making it unfit for multiple patient use. Moving the opening farther away from the patient—for example, by way of a pneumatic tube connected to the casing—still results in a contagion pathway.

Still yet another disadvantage of an electronic monitor is its stiffness, which contributes to patient discomfort. A certain amount of stiffness is required in the outer casing and the spacer to keep the electrodes from coming into contact with one another absent external pressure. Even if the outer casing is composed of a softer, more flexible material, the spacer still needs to retain its stiffness to keep the electrodes apart.

The disadvantages of electronic monitors have led to attempts to produce pneumatic patient bed monitors. Similar to an electronic monitor, the pneumatic monitor senses an initial status of the patent and generates a signal when that status changes. Although this type of monitor may be used in almost any patient environment, the various designs proposed to date have serious flaws. Because the monitor relies upon an air-filled envelope, it lacks a precise triggering event and is susceptible to high frequency response due to the patient shifting within the bed or chair. Attempts to control high frequency response have involved the use of stiffer casings and pressure plates, all of which significantly decrease patient comfort. Additionally, the monitor is subject to leaks, which trigger false alarms, and therefore must be equipped with an inflation valve. The valve, in turn, becomes another potential failure point. Because of these and other problems, no pneumatic patient bed monitor is manufactured or sold. A need exists, therefore, for an improved pneumatically operated patient bed monitor.

SUMMARY OF THE INVENTION

A pneumatic patient bed monitor comprises a hermetically sealed flexible outer shell that contains a porous foam core having a certain volume of air. A flexible tube places the foam core in communication with a pneumatic pressure switch. The pressure switch is in a normally open position. When a weight of a patient compresses the foam core, air contained in the foam core flows in a controlled manner into the tube, thereby causing a rise in pressure within the tube and actuating the pressure switch. When the weight of the patient is removed, air flows out of the tube in a controlled manner and back into the foam core, causing a drop in pressure within the tube and de-actuating the pressure switch. The foam core returns to its decompressed state. The foam core serves to dampen high frequency response caused by the patient shifting within the bed. The core controls the flow of air into and out of the tube and causes a delay in the actuation or de-actuation of the pressure switch as the outer shell is placed under load and relieved of load, respectively. Because the foam core gives shape to the outer shell during assembly of the monitor, the core will always contain a certain amount of air, thereby eliminating the need for an inflation valve. Foam core will always return or rebound to atmospheric pressure when relieved of load.

When the bed monitor is placed under a mattress, a weight of a patient on the mattress compresses the foam core, air flows in a controlled manner out of the foam core and into the tubing, leading to a rise in pressure in the tube and causing the pressure switch to close. When the weight of the patient is removed, air flows out of the tubing in a controlled manner, leading to a drop in pressure causing the pressure switch to open. The foam core returns to its decompressed condition.

BRIEF DESCRIPTION OF THE DRAWING

Other objects and advantages of this invention will become apparent upon reading the following detailed description and upon reference to the drawings in which.

DETAILED DESCRIPTION

Figure 1:
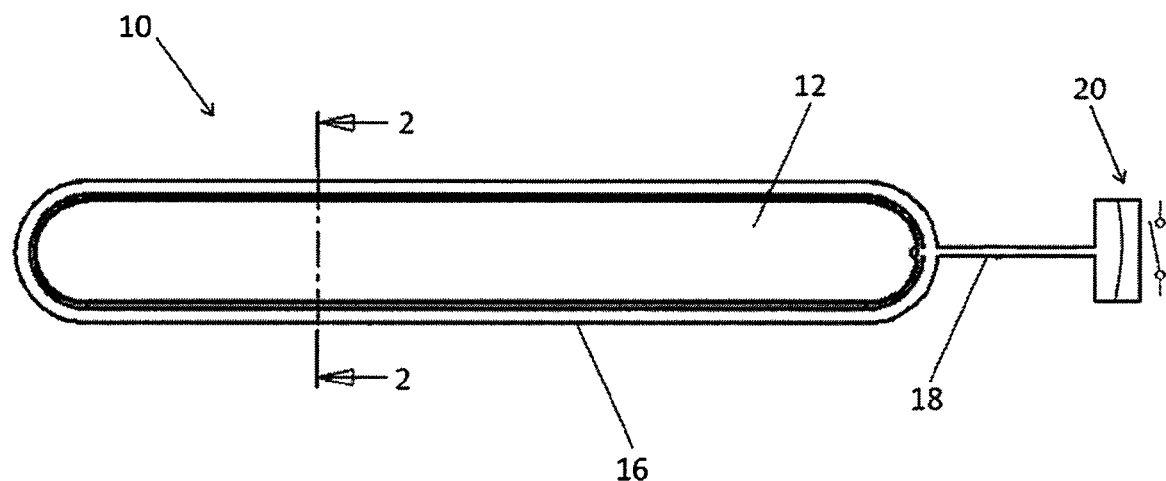
FIG. 1 is a top view of a pneumatic patient bed monitor having a porous foam core and connected by flexible tubing to a pneumatic pressure switch.
Figure 2:
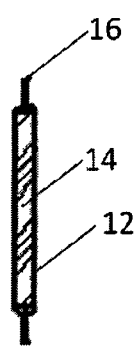
FIG. 2 is a view taken along section line 2-2 of FIG. 1 and showing the porous foam core contained within the flexible outer shell.

Referring to FIGS. 1 and 2, a patient bed monitor 10 comprises a flexible outer shell 12, a porous foam core 14, a flexible tubing 18, and a pneumatic pressure switch 20. Outer shell 12 is preferably a vinyl material and is hermetically sealed along its outer perimeter 16. Alternatively, outer shell 12 may be a urethane material. Further, heat, ultrasonic, radio frequency, a dielectric means may be used to seal shell 12 along its outer perimeter 16. Tube 18 places foam core 14 in communication with pressure switch 20 and is hermetically sealed to outer shell 12 and switch 20. Pressure switch 20 is normally open and connected to an alarm system (not shown). In a preferred embodiment, pressure switch 20 further comprises a cable (not shown) that provides for its use with existing bed monitor enunciators. An adaptor plug (not shown) may also be provided for use with enunciators in certain international markets such as the United Kingdom.

Foam core 14 provides stability to bed monitor 10 when bed monitor 10 is under a patient load and serves to dampen high frequency response caused by the patient shifting within the bed. Foam core 14 is preferably in a range of ⅜ to ½ inch thick and comprised of open cells, each cell being interconnected to neighboring cells. The cells preferably have a pore size in a range of 50 to 100 pores per inch. By specifying the indentation load deflection and density of foam core 14 to a predetermined value, core 14 works to slow the flow of air to pressure switch 20, thereby controlling high frequency response. Preferably, the compression of core 14 is set at 50% deflection in a range of 4% to 8% maximum. Limiting the compression set of the foam core 14 to 50% helps assure that the foam core 14 rebounds close to its original volume when the patent's weight is removed from the bed. Air flowing back into the foam core 14 relieves the pressure holding the normally open pressure switch 20 closed. Further, the preferred foam density is in a range of 1.6 to 2.5 lbs/ft$^3$. Unlike an air-filled envelope which cannot control for high frequency response, foam core 14 causes a delay in the actuation or de-actuation of pressure switch 20 as outer shell 12 is placed under load and relieved of load, respectively.

Because foam core 14 gives shape to outer shell 12 during assembly, it will always contain a certain amount of air. There is no need for an inflation valve. Once outer shell 12 is hermetically sealed to tube 18, and tube 18 is hermetically sealed to pressure switch 20, foam core 14 has atmospheric pressure in it and will always return or rebound to atmospheric pressure when relieved of load.

When bed monitor 10 is placed under a mattress, a weight of a patient on the mattress compresses foam core 14, leading to a rise in pressure in tubing 18 and causing pressure switch 20 to close. Air flows in a controlled manner out of foam core 14 and into tube 18. When the weight of the patient is removed, pressure in tubing 18 is relieved and the air flows out of tube 18 in a controlled manner. This fall in pressure on foam core 14 causes pressure switch 20 to open, triggering the alarm. Foam core 14 returns to its decompressed condition.

While this invention has been described in conjunction with a specific embodiment thereof, it is evident that many alternatives, modifications and variations will be apparent to those skilled in the art and in light of the foregoing description. Accordingly, it is intended to embrace all such alternatives, modifications, and variations as fall within the scope of the appended claims.

What is claimed is:

1. A patient monitor alarm system comprising:
a hermetically sealed flexible enclosure;
a pneumatic pressure switch having a predetermined actuating pressure;
a foam core being contained within the enclosure;
a tube connecting the foam core to the pressure switch and being hermetically sealed to the enclosure and the pressure switch; and
a remote alarm signal that is actuated by the switch;
wherein a weight of a patient compresses the foam core and raises a pressure within the tube above a predetermined level, thereby causing the pressure switch to actuate.

2. A patient monitor alarm system according to claim 1, the pressure switch being normally open.

3. A patient monitor alarm system according to claim 1, the foam core being an open-cell foam.

4. A patient monitor alarm system according to claim 3, the foam core containing a predetermined volume of air.

5. A patient monitor alarm system according to claim 3, the foam core being in a range of ⅜ inch to ½ inch in thickness.

6. A patient monitor alarm system according to claim 3, the foam core having a density in a range of 1.6 to 2.5 lbs/ft$^3$.

7. A patient monitoring system according to claim 3, the foam core having a compression set at 50% deflection in a range of 4% to 8% maximum.

8. A patient monitoring system according to claim 3, the foam core having a pore size in a range of 50 to 100 pores per inch.

9. A patient monitor alarm system according to claim 1, the flexible enclosure being vinyl.

10. A patient monitor alarm system according to claim 1, the flexible enclosure being urethane.

11. A patient monitor alarm system according to claim 1, the flexible enclosure being heat sealed.

12. A patient monitor alarm system according to claim 1, the flexible enclosure being ultrasonically welded.

13. A patient monitor alarm system according to claim 1, the flexible enclosure being radio frequency sealed.

14. A patient monitor alarm system according to claim 1, the flexible enclosure being dielectrically sealed.

* * * * *